United States Patent [19]

Jongenburger

[11] Patent Number: 5,489,366

[45] Date of Patent: Feb. 6, 1996

[54] RECOVERY OF PURIFIED AND SUBSTANTIALLY ANHYDROUS PROPYLENE OXIDE

[75] Inventor: Huibert S. Jongenburger, Houston, Tex.

[73] Assignee: Texaco Chemical Inc., White Plains, N.Y.

[21] Appl. No.: 219,043

[22] Filed: Mar. 28, 1994

[51] Int. Cl.⁶ .......................... B01D 3/40; C07D 301/32
[52] U.S. Cl. .................. 203/14; 203/33; 203/36; 203/37; 203/41; 203/52; 203/70; 203/73; 203/80; 549/541; 549/542
[58] Field of Search ................ 203/70, 41, 52, 203/14, 71, 73, 80, 36, 37, 33; 549/541, 542

[56] References Cited

U.S. PATENT DOCUMENTS

| | | | |
|---|---|---|---|
| 2,622,060 | 12/1952 | Robeson et al. | 203/37 |
| 3,066,116 | 11/1962 | Schiller et al. | 203/41 |
| 3,282,966 | 11/1966 | Naugle | 203/14 |
| 3,350,418 | 10/1967 | Bowe et al. | 203/70 |
| 3,477,919 | 11/1969 | Lichtenwalter et al. | 549/572 |
| 3,607,669 | 9/1971 | Jubin | 203/70 |
| 4,691,034 | 9/1987 | Sanderson et al. | 549/542 |
| 4,691,035 | 9/1987 | Sanderson et al. | 549/542 |
| 4,772,732 | 9/1988 | Huang et al. | 549/542 |
| 5,106,458 | 4/1992 | Meyer et al. | 549/542 |
| 5,133,839 | 7/1992 | Shih | 203/70 |
| 5,187,287 | 2/1993 | Shih | 549/542 |
| 5,354,430 | 10/1994 | Culbreth et al. | 549/541 |

Primary Examiner—Wilbur Bascomb, Jr.
Attorney, Agent, or Firm—James L. Bailey; Kenneth R. Priem; Carl G. Ries

[57] ABSTRACT

A distillation method for the purification of crude propylene oxide containing contaminating quantities of water and methanol by partially purifying the crude propylene oxide in a plural stage distillation zone to provide a vaporized overhead distillate propylene oxide fraction containing a minor contaminating amount of vaporized water, and passing the propylene oxide vapor fraction through a drying chamber containing a porous hygroscopic solid absorbent to selectively absorb water vapor onto the absorbent, and liquefying and recovering the thus-dehydrated purified propylene oxide.

17 Claims, 1 Drawing Sheet

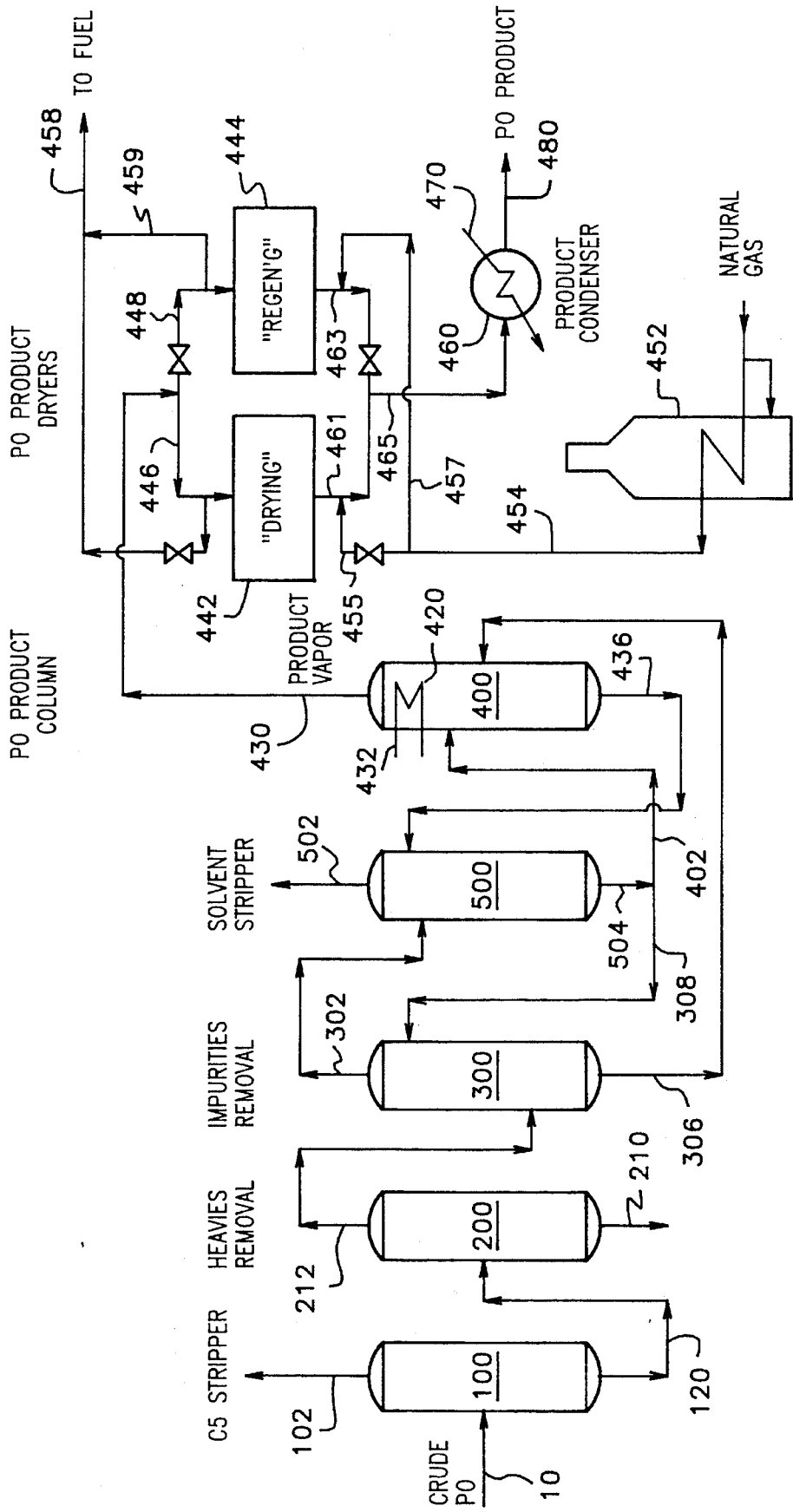

5,489,366

RECOVERY OF PURIFIED AND SUBSTANTIALLY ANHYDROUS PROPYLENE OXIDE

BACKGROUND OF THE INVENTION

1. Field of the Invention

This invention relates to the purification of crude propylene oxide. More particularly, this invention relates to a distillation process for removing contaminating quantities of methanol, acetone, and water from a crude propylene oxide feedstock. Still more particularly this invention relates to a method wherein a crude propylene oxide feedstock contaminated with from about 50 to about 1000 ppm of methanol, from about 0 to 1 wt. % of acetone and about 0.4 to about .4 wt. % of water is partially purified in a distillation zone comprising a plurality of distillation columns to obtain a vaporized overhead propylene oxide distillate fraction consisting essentially of propylene oxide and about 0.04 to about 0.8 wt. % of water wherein the vaporized distillate fraction is passed through a drying chamber containing a porous hygroscopic solid absorbent to selectively absorb water vapor onto the absorbent, and wherein the thus-dehydrated purified propylene oxide is liquefied and recovered.

2. Prior Art

It is known to react a hydroperoxide feedstock such as tertiary butyl hydroperoxide with propylene in the presence of an epoxidation catalyst in order to provide a reaction product comprising propylene oxide, an alcohol corresponding to the hydroperoxide feedstock, a solvent, and impurities (see, for example, Kollar U.S. Pat. No. 3,350,422, Kollar U.S. Pat. No. 3,351,635 and Sorgenti U.S. Pat. No. 3,666,777.

It is also known to separate the reaction product by distillation in order to obtain a plurality of fractions including, for example, a propylene recycle fraction, a propylene oxide product fraction, an alcohol fraction, etc.

It is also known that methanol is a common contaminant for propylene oxide which is removed only with difficulty.

For example, Mitchell et al. U.S. Pat. No. 2,550,847 is directed to a process for separating purified propylene oxide from a crude propylene oxide product contaminated with acetaldehyde, methyl formate, methanol, etc., by treating the crude mixture with an aqueous basic substance followed by recovery of the purified propylene oxide by any suitable means such as by decantation. Mitchell et al. reported a recovery of a product containing 78 to 82 wt. % of propylene oxide which, they stated, could be increased in purity to about 95 to 99% by fractional distillation.

Robeson et al. U.S. Pat. No. 2,622,060 discloses a process for the purification of propylene oxide contaminated with impurities, including methanol, by subjecting the impure propylene oxide to distillation in the presence of an extractive distillation agent comprising an aqueous solution of an alkali. The inventors report in Example 1 of their patent a method wherein 500 parts by weight of a crude propylene oxide fraction was extractively distilled in accordance with their invention to obtain 325 parts by weight of a product containing about 99.6 wt. % of propylene oxide. Thus, a significant loss of propylene oxide occurred during the process.

In a process unrelated to the purification of propylene oxide, Goddin et al. in U.S. Pat. No. 2,751,337 disclose a process for separating acetone from a mixture of acetone with methanol and methyl acetate utilizing water as an extractive distillation agent.

Hamlin et al. in U.S. Pat. No. 3,409,513 disclose the hydro-extractive distillation of mixtures comprising acetone, lower aliphatic alcohols and esters of lower aliphatic alcohols with carboxylic acids. It is pointed out by the patentees that acetone, methyl acetate and methanol form an azeotrope boiling at 55.5–56.5–C. Hamlin et al. propose to recover partially purified acetone from such a ternary azeotrope by liquid-liquid extraction with water followed by hydro-extractive distillation of the aqueous phase in order to obtain a partially purified acetone fraction.

Washall U.S. Pat. No. 3,578,568 discloses a process for removing oxygen-containing impurities such as acetone, acetaldehyde and methanol from impure propylene oxide using a glycol such as ethylene glycol or propylene glycol as an extractive distillation agent.

Heary and Newman U.S. Pat. No. 3,632,482 is directed to a propylene oxide recovery process by extractive distillation using an alcohol-ketone-hydrocarbon solvent. The invention relates to a method for the purification of crude propylene oxide contained in a mixture produced by the epoxidation of propylene with an organic hydroperoxide and calls for extractive distillation of the crude propylene oxide in a plurality of successive extractive distillation zones with the aid of a solvent mixture consisting essentially of hydrocarbons, alcohols, and/or ketones corresponding to the organic hydroperoxide employed in producing the propylene oxide. In the preferred embodiment of their invention, the extractive distillation agent is a recycle fraction from a three column distillation sequence wherein the bottoms from the third distillation column are flashed to obtain an overhead composed of hydrocarbons, alcohols and/or ketones which is recycled as an extractive distillation agent to the three distillation columns involved in the propylene oxide purification sequence.

Burns et al. U.S. Pat. No. 3,715,284 discloses a process for the purification of impure propylene oxide using acetone or a mixture of acetone with methanol which is introduced into a distillation column either below or together with the impure propylene oxide.

Schmidt U.S. Pat. No. 3,881,996 is directed to a distillation sequence employing at least three and optionally four columns for the purification of crude propylene oxide, one of the columns optionally being an extractive distillation column wherein a hydrocarbon such as octane is used as the extractive distillation agent.

Schmidt U.S. Pat. No. 4,140,588 discloses a process for the purification of propylene oxide contaminated with methanol and acetone using water as an extractive distillation agent, the water being introduced into the distillation column above the point of introduction of the crude propylene oxide feed.

Schmidt states at column 2, lines 50–55 that: "Propylene oxide, however, has a substantial solubility in water and is readily hydrolyzed to propylene glycol (PG) in the presence of large amounts of water"—i.e., in the reboiler section of the tower.

The presence of additional acetone (added to feed or solvent) in accordance with the present invention serves as a buffer between the reboiler section and the balance of the tower. This is apparent if one looks at the normal boiling points (i.e., atmospheric pressure):

| Component | NBP (°C.) |
| --- | --- |
| Propylene Oxide (PO) | 34 |
| Acetone | 56 |
| Water | 100 |

The acetone serves as a buffer section in the tower between the PO and water (a high concentration of water is in the reboiler and a high concentration of PO is above the acetone buffer zone). The acetone buffer zone limits the contact of PO with a high concentration of water. It is apparent that the additional acetone makes its presence known in the reboiler as well as evidenced by lower reboiler temperatures. This also helps reduce PO to PG conversion as the reaction rate increases with increasing temperature. Any PO making its way to the reboiler will see a lower temperature, thus reducing its conversion to PG.

It is clear that the tower should be operated at as low a pressure as is practical to minimize PO loss.

Seifert et al. U.S. Pat. No. 4,369,096 is directed to a process for the purification of epoxides wherein the purification is effected by treatment with compounds containing at least one primary amine group.

BACKGROUND OF THE PRESENT INVENTION

When propylene is reacted in liquid phase with an organic hydroperoxide such as tertiary butyl hydroperoxide in solution in a solvent such as tertiary butyl alcohol in the presence of a soluble epoxidation catalyst such as a molybdenum epoxidation catalyst, a reaction mixture is formed comprising propylene oxide, an alcohol corresponding to the organic hydroperoxide feedstock and impurities including water and other oxygenated impurities such as methyl formate, acetaldehyde, acetone and methanol.

Propylene oxide is a hygroscopic substance, so that water is removed only with difficulty. It is important to remove as much of the water as possible, however, because propylene oxide will tend to react with water to form propylene glycol.

It is also important to reduce the level of other oxygenated contaminants such as methanol and acetone to the lowest reasonably attainable level.

In accordance with conventional practice, an epoxidation reaction product formed by the molybdenum-catalyzed reaction of propylene oxide with tertiary butyl hydroperoxide in solution in tertiary butyl alcohol is separated into the principle components by distillation so as to form distillation fractions including a propylene distillation fraction, a propylene oxide distillation fraction, a tertiary butyl alcohol distillation fraction and a heavy distillation fraction containing the molybdenum catalyst and other products and by-products of the epoxidation reaction. However, the distillation fractions that are thus-obtained are characterized by the inclusion of impurities and, normally, must be further treated if commercially acceptable products are to be obtained. This is especially true for a propylene oxide distillation fraction contaminated with water and oxygenated contaminants including methanol and acetone. Other oxygen-containing contaminants are normally present, including acetaldehyde, methyl formate, tertiary butyl alcohol, and $C_5$ and $C_6$ hydrocarbons. Normally, primary emphasis is placed on early removal of water and methanol because their boiling characteristics make their removal particularly difficult.

Typically, a distillation train is used wherein acetaldehyde, methyl formate and $C_5$ hydrocarbons are removed overhead from the crude propylene oxide in a first distillation column to provide a heavier distillation propylene oxide fraction from which oxygen-containing impurities including methanol, acetone, tertiary butyl alcohol and water are removed by extractive distillation using a glycol or glycol ether type extractive distillation agent, as shown, for example in Shih et al. U.S. Pat. No. 5,000,825. Thereafter, the $C_6$ hydrocarbons are removed by a separately conducted extractive distillation step using a $C_8$ to $C_{10}$ paraffinic hydrocarbon extractive distillation agent.

It has been surprisingly discovered in accordance with the present invention that the need to use two separate extractive distillation stages with different extractive distillation agents in each stage can be obviated and that only one extractive distillation step is necessary, using a $C_8$ to $C_{10}$ paraffinic hydrocarbon extractive distillation agent, provided that the distillation conditions are properly adjusted in the other distillation columns comprising the distillation train so that water and methanol can be progressively removed as the propylene oxide passes through the distillation train for purification.

SUMMARY OF THE INVENTION

In accordance with the present invention, the purification of crude propylene oxide containing contaminating quantities of water, acetaldehyde and methanol and other impurities is accomplished in a plural stage distillation zone to provide a final vaporized overhead distillate propylene oxide fraction consisting essentially of propylene oxide and a minor contaminating amount of vaporized water; the propylene oxide vapor fraction being passed through a drying chamber containing a porous hygroscopic solid absorbent to selectively absorb water vapor onto the absorbent, and the thus-dehydrated purified propylene oxide then being liquefied and recovered.

In accordance with a preferred embodiment of the present invention, crude propylene oxide containing contaminating quantities of water, acetaldehyde, and methanol is purified in a plural stage distillation zone by:

charging the crude propylene oxide to a first distillation column and operating the first distillation column under distillation conditions of temperature and pressure selected to provide a first lighter liquid distillation fraction comprising acetaldehyde and a first heavier liquid distillation fraction comprising propylene oxide, water and methanol, charging the first heavier distillation fraction to a second distillation column and operating the second distillation column under distillation conditions of temperature and pressure selected to provide a second lighter liquid distillation fraction comprising propylene oxide, less than half of the water charged to the second distillation column and more than half of the methanol charged to the second distillation column and a second heavier liquid distillation fraction comprising more than half of the water charged to the second distillation column and less than half of the methanol charged to the second distillation column, charging the second lighter distillation fraction to a third extractive distillation column and also charging an effective amount of a $C_8$ to $C_{10}$ paraffinic hydrocarbon extractive distillation agent thereto and operating the third distillation column under extractive distillation conditions of temperature and pressure selected to provide a third lighter liquid distillation fraction comprising the extractive distillation agent, substantially less than 50% of the water and substantially all of the methanol charged to the third distillation column and a third heavier liquid distillation fraction comprising propylene oxide and less than half of the water charged to the third distillation column, charging the third heavier distillation fraction to a fourth extractive distillation column and also charging an effective amount of a $C_8$ to $C_{10}$ paraffinic hydrocarbon extractive distillation agent hereto and operating the fourth distillation column under extractive distillation conditions of temperature and pressure selected to provide a fourth lighter vapor overhead distillate fraction comprising propylene oxide and less than half of the water charged to the fourth distillation column and a fourth heavier liquid distillation fraction comprising the extractive distillation agent and more than half of the water charged to the fourth distillation column, passing said propylene oxide vapor fraction through a drying chamber containing a porous hygroscopic solid absorbent at a temperature of about 30° to about 100° C. and a pressure of about 15 to about 30 psia, to selectively absorb water vapor onto the absorbent, and liquefying and recovering the thus-dehydrated purified propylene oxide.

In accordance with a preferred specific embodiment of the present invention, crude propylene oxide containing contaminating quantities of water, $C_5$ and $C_6$ hydrocarbons, methyl formate, acetaldehyde, methanol, tertiary butyl alcohol and acetone is purified in a plural stage distillation zone by:

charging the crude propylene oxide to a first distillation column and operating the first distillation column under distillation conditions of temperature and pressure selected to provide a first lighter liquid distillation fraction comprising $C_5$ hydrocarbons, methyl formate and acetaldehyde and a first heavier liquid distillation fraction comprising propylene oxide, water, methanol, propionaldehyde, tertiary butyl alcohol, acetone, methyl formate acetaldehyde and $C_6$ hydrocarbons, charging the first heavier distillation fraction to a second distillation column and operating the second distillation column under distillation conditions of temperature and pressure selected to provide a second lighter liquid distillation fraction comprising propylene oxide, less than half of the water charged to the second distillation column, more than half of the methanol charged to the second distillation column, methyl formate, acetaldehyde and $C_6$ hydrocarbons, and a second heavier liquid distillation fraction comprising more than half of the water charged to the second distillation column, less than half of the methanol charged to the second distillation column, propionaldehyde, acetone and tertiary butyl alcohol, charging the second lighter distillation fraction to a third extractive distillation column and also charging an effective amount of a $C_8$ to $C_{10}$ paraffinic hydrocarbon extractive distillation agent thereto and operating the third distillation column under extractive distillation conditions of temperature and pressure selected to provide a third lighter liquid distillation fraction comprising the extractive distillation agent, more than half of the water charged to the third distillation column, substantially all of the methanol charged to the third distillation column, methyl formate and acetaldehyde and a third heavier liquid distillation fraction comprising propylene oxide, less than half of the water charged to the third distillation column, and $C_6$ hydrocarbons, charging the third heavier distillation fraction to a fourth extractive distillation column and also charging an effective amount of a $C_8$ to $C_{10}$ paraffinic hydrocarbon extractive distillation agent hereto and operating the fourth distillation column under extractive distillation conditions of temperature and pressure selected to provide a fourth lighter vapor overhead distillate fraction comprising propylene oxide and less than half of the water charged to the fourth distillation column and a fourth heavier liquid distillation fraction comprising the extractive distillation agent, more than half of the water charged to the fourth distillation column, and $C_6$ hydrocarbons, passing said propylene oxide vapor fraction through a drying chamber containing a porous hygroscopic solid absorbent at a temperature of about 30° to about 100° C. and a pressure of about 15 to about 30 psia, to selectively absorb water vapor onto the absorbent, and liquefying and recovering the thus-dehydrated purified propylene oxide.

BRIEF DESCRIPTION OF THE DRAWING

The drawing is a schematic flow sheet with conventional parts omitted showing the general recovery sequence that is used in accordance with the present invention in purifying propylene oxide.

In the drawing, for convenience, the present invention is illustrated in connection with a process wherein the crude propylene oxide is prepared by the epoxidation of propylene with tertiary butyl hydroperoxide to provide a reaction product comprising propylene oxide, additional tertiary butyl alcohol and impurities, principally oxygen-containing by-products.

DESCRIPTION OF THE PREFERRED EMBODIMENT

Turning now to the drawing, there is shown a schematic flow sheet illustrating a preferred method of practicing the process of the present invention. In the drawing, conventional parts such as valves, pumps, temperature sensors, pressure sensors, heaters, coolers, flow control regulation apparatus, reboilers, reflux condensers, etc., have been omitted.

In accordance with a preferred embodiment of the present invention, propylene oxide is separated from other components of an epoxidation reaction mixture in order to provide a crude propylene oxide fraction contaminated with water and with oxygen-containing impurities such as propionaldehyde, acetaldehyde, methyl formate, acetone, methanol, tertiary butyl alcohol, etc., and with $C_5$ and $C_6$ hydrocarbons.

The crude propylene oxide feedstock that is thus provided is then purified in a distillation zone, which in accordance with the preferred embodiment of the present invention, comprises a plurality of distillation columns, each of which is equipped with an appropriate reflux condensing means and an appropriate reboiler heating means.

Thus, in accordance with the present invention, an impure propylene oxide fraction, or crude propylene oxide, contaminated with impurities including methyl formate, acetaldehyde, propionaldehyde, acetone, methanol and water is charged by a charge line 10 to a first distillation column 100 which is operated so as to remove methyl formate, acetaldehyde and $C_5$ hydrocarbons as an overhead distillate fraction by way of a discharge line 102. In accordance with this embodiment, the first distillation column 100 will suitably contain about 10 to 60 theoretical plates and is operated at a pressure of about 10 to about 70 psig. with a reboiler temperature of about 50° to about 90° C. and a top reflux temperature of about 40° to about 80° C., the distillation conditions being selected so as to obtain substantially complete removal of the $C_5$ hydrocarbons and partial removal of acetaldehyde and methyl formate impurities overhead by way of a line 102.

The heavier distillation fraction 120 discharged from the column 100, comprises substantially all of the propylene oxide charged to the distillation column 100 by the charge line 10 and is contaminated with from about 50 to 4,000 ppm of methanol, from about 0 to 2 wt. % of acetone, from about 0.04 to about 4 wt. % of water and other contaminants, including $C_6$ hydrocarbons, acetaldehyde, propionaldehyde, tertiary butyl alcohol, etc., the heavier fraction being discharged by way of a line 120 leading to a second distillation column 200 which, in accordance with the present invention, will preferably be a column containing at least about 25 theoretical plates and more preferably, from about 30 to about 100 theoretical plates. The column 200 is suitably operated under distillation conditions including a pressure of about 0 to 30 psig., a reflux ratio of from about 5:1 to about 10:1, a reboiler temperature within the range of about 100° to about 135° C. and a top temperature of about 35° to about 70° C.

Within the distillation column 200, more than 50% of the water and less than 50% of the methanol introduced into the column 200 by the line 120 are removed as a heavier distillation fraction 210 together with propionaldehyde, acetone and tertiary butyl alcohol and a partially purified propylene oxide distillate fraction is removed overhead by a line 212, the partially purified propylene oxide distillate fraction 212 containing the remaining portions of the water and methanol and also contaminants including $C_6$ hydrocarbons, acetaldehyde and methyl formate.

In accordance with the present invention, the partially purified propylene oxide fraction 212 is charged by way of line 212 to a distillation column 300 which, in accordance with the present invention, will preferably be a column containing at least about 10 theoretical plates and more preferably, from about 30 to about 100 theoretical plates. The column 300 is suitably operated under distillation conditions including a pressure of about 10 to 40 psia, a reflux ratio of from about 2:1 to about 10:1, a reboiler temperature within the range of about 100° to about 250° C. (e.g., 210° C.) and a top temperature of about 20° to about 80° C. (e.g., about 20° C.).

The impure propylene oxide is preferably charged to the distillation column 300 in the lower half thereof. An extractive distillation agent, comprising a $C_8$ to $C_{10}$ paraffinic hydrocarbon, such as isooctane, is charged to the upper half of the distillation column 300 by an extractive distillation charge line 308.

A liquid overhead fraction is removed from the distillation column 300 by an overhead line 302. The overhead fraction 302 will comprise substantially all of the methanol charged to the column 300, substantially less than 50% of the water and substantially all of the methanol charged to the column 300, acetaldehyde, methyl formate and the paraffinic hydrocarbon stripping agent. The bottom fraction 306 will comprise propylene oxide, more than 50 wt. % of the water charged to the column 300 and the $C_6$ hydrocarbon contaminants.

In accordance with the present invention, the third heavier distillation fraction 306 is charged to a fourth extractive distillation column 400 together with an extractive distillation agent, such as a $C_8$ to $C_{10}$ paraffinic hydrocarbon (e.g., isooctane), which is charged by a line 402. The extractive distillation agent may suitably be charged to the distillation column 400 in the ratio of about 0.4 to about 0.8 part of extractive distillation agent per part of heavier distillation fraction 306. The fourth distillation column 400 will preferably be a column containing at least 10 theoretical plates and, more preferably, from about 30 to 100 theoretical plates and is suitably operated under distillation conditions including a pressure of about 10 to 40 psia, a reboiler temperature within the range of about 100° to about 250° C. (e.g., about 210° C.) and a top temperature of about 20° to about 80° C. (e.g., 20° C.).

The fourth extractive distillation column 400 of the present invention is provided with suitable internal cooling means, such as a condenser coil 420 located adjacent the top of the column 400. A suitable coolant, such as water, may be flowed through the condenser coil 420 at a rate sufficient to partially condense the distillate vapors at the top of the column 400 before they are discharged therefrom by a vapor line 430. With this construction, the condenser coil 420 is operated so as to serve, in effect, as an internal reflux condenser.

The overhead vapor fraction 430 obtained in this fashion will consist essentially of pure vaporized propylene oxide, but a minor amount of vaporized water will still be present. In accordance with the present invention, the vaporized propylene oxide fraction 430, containing about 50 to 500 ppm of water is charged to a dehydration zone 440 of any suitable construction.

For example, the dehydration zone 440 may comprise a pair of drying chambers 442 and 444 connected in parallel with the line 430 by inlet lines 446 and 448, respectively. Each of the chambers 442–444 will contain a bed of a porous hygroscopic solid absorbent such as a molecular sieve (e.g., 3A or 4A), an alkali metal or alkaline earth metal oxide or hydroxide such as calcium oxide, potassium hydroxide, etc., a hygroscopic alkaline earth metal sulfate or alkali metal sulfate such as calcium sulfate, sodium sulfate hemihydrate, etc.), silica gel, etc.

The overhead vapor fraction 430 is charged to one of the drying chambers 442–444 (e.g., 442) by branch line 446 where the residual water is absorbed to thereby provide a substantially completely dehydrated purified propylene oxide vapor product fraction 461. When the chamber 442 loses drying efficiency (e.g., becomes saturated with water), the vaporized propylene oxide fraction is charged to the other drying chamber 444 by the charge line 448 and the drying chamber 442 is regenerated. This can be accomplished, for example, by charging a hot regeneration gas, such as natural gas which is heated in a furnace 452 and discharged therefrom by a line 454 for sequential backflow through the drying chambers 442–444 through backflow charge lines 455–457, respectively, and then through backflow discharge lines 458–459, respectively.

The dehydrated propylene oxide vapor is discharged from drying chambers 442–444 by discharge lines 461–463, respectively, which lead to a condenser charge line 465 leading to a condenser 460 where the vaporized propylene oxide is liquefied in any suitable manner, such as by indirect counter-current contact with a cooling liquid (e.g., water), passed through the condenser 460 by a line 470. The liquefied, purified, dehydrated propylene oxide is discharged from the condenser, as the final product by a line 480 leading to a suitable storage facility (not shown).

The lighter distillation fraction 302 and a heavier distillation fraction 436 suitably may be charged to a fifth distillation column 500 which may comprise, for example, from about 30 to about 50 theoretical trays. Distillation conditions are adjusted within the distillation column 500 to provide for the recovery of a lighter distillation fraction 502 comprising acetaldehyde, methanol, methyl formate, $C_6$ hydrocarbons, etc., and a heavier distillation fraction 504 comprising substantially all of the extractive distillation agent charged to the distillation column 500. For example, distillation conditions in the fifth distillation column 500 may include a pressure at the top of the column of about 15 to 30 psia and a temperature of about 100°–140° F. and a pressure at the bottom of the column of about 20–40 psia and a temperature of about 200°–300° F.

An appropriate portion of the heavier distillation fraction 504 may be returned to the column 300 for recycled use as an extractive distillation agent by line 308 and the remainder of the fraction 504 may be recycled to the distillation column 400 for use therein as extractive distillation agent 402.

Having this described our invention, what is claimed is:

1. In a distillation method for the purification of crude propylene oxide containing contaminating quantities of water, acetaldehyde and methanol wherein the crude propylene oxide is partially purified in a plural stage distillation zone to provide a vaporized overhead distillate propylene oxide fraction consisting essentially of propylene oxide and not more than about 0.2 wt. % of vaporized water, the improvement which comprises the step of:

passing said propylene oxide vapor fraction through a drying chamber containing a porous hygroscopic solid absorbent at a temperature of about 34° to about 100° C. and a pressure of about 15 to about 30 psia, to selectively absorb water vapor onto the absorbent, and liquefying and recovering the thus-dehydrated purified propylene oxide.

2. A method as in claim 1 wherein the porous hygroscopic solid absorbent is a molecular sieve.

3. A method as in claim 2 wherein the molecular sieve is type 3A.

4. A distillation method for the purification of crude propylene oxide containing contaminants comprising water, acetaldehyde and methanol which comprises the steps of:

charging the crude propylene oxide to a first distillation column and operating the first distillation column under distillation conditions of temperature and pressure selected to provide a first lighter liquid distillation fraction comprising acetaldehyde and a first heavier liquid distillation fraction comprising propylene oxide, water and methanol, charging the first heavier distillation fraction to a second distillation column and operating the second distillation column under distillation conditions of temperature and pressure selected to provide a second lighter liquid distillation fraction comprising propylene oxide, less than half of the water charged to the second distillation column and more than half of the methanol charged to the second distillation column and a second heavier liquid distillation fraction comprising more than half of the water charged to the second distillation column and less than half of the methanol charged to the second distillation column, charging the second lighter distillation fraction to a third extractive distillation column and also charging an effective amount of a $C_8$ to $C_{10}$ paraffinic hydrocarbon extractive distillation agent thereto and operating the third distillation column under extractive distillation conditions of temperature and pressure selected to provide a third lighter liquid distillation fraction comprising the extractive distillation agent, substantially less than 50% of the water charged to the third distillation column and substantially all of the methanol charged to the third distillation column and a third heavier liquid distillation fraction comprising propylene oxide and than less than half of the water charged to the third distillation column, charging the third heavier distillation fraction to a fourth extractive distillation column and also charging an effective amount of a $C_8$ to $C_{10}$ paraffinic hydrocarbon extractive distillation agent thereto and operating the fourth distillation column under extractive distillation conditions of temperature and pressure selected to provide a fourth lighter vapor overhead distillate fraction comprising propylene oxide and less than half of the water charged to the fourth distillation column and a fourth heavier liquid distillation fraction comprising the extractive distillation agent and more than half of the water charged to the fourth distillation column, passing said propylene oxide vapor fraction through a drying chamber containing a porous hygroscopic solid absorbent at a temperature of about 34° to about 100° C. and a pressure of about 15 to about 30 psia, to selectively absorb water vapor onto the absorbent, and liquefying and recovering the thus-dehydrated purified propylene oxide.

5. A method as in claim 4 wherein the porous hygroscopic solid absorbent is a molecular sieve.

6. A method as in claim 5 wherein the molecular sieve is type 3A.

7. A method as in claim 4 wherein the porous hygroscopic solid absorbent is a hygroscopic alkali metal or alkaline earth metal oxide or a hygroscopic alkali metal or alkaline earth metal hydroxide compound.

8. A method as in claim 7 wherein the alkaline earth metal oxide is calcium oxide.

9. A method as in claim 7 wherein the alkali metal hydroxide is potassium hydroxide.

10. A method as in claim 4 wherein the porous hygroscopic solid absorbent is a hygroscopic alkali metal sulfate or an alkaline earth metal sulfate.

11. A method as in claim 10 wherein the porous hygroscopic alkali metal sulfate compound is sodium sulfate.

12. A method as in claim 10 wherein the porous hygroscopic alkaline earth metal sulfate compound is calcium sulfate.

13. A method as in claim 10 wherein the porous hygroscopic alkali metal sulfate compound is sodium sulfate hemihydrate.

14. A distillation method for the purification of crude propylene oxide containing contaminating quantities of water, $C_5$ and $C_6$ hydrocarbons, methyl formate, acetaldehyde, propionaldehyde, methanol, tertiary butyl alcohol and acetone which comprises the steps of:

charging the crude propylene oxide to a first distillation column and operating the first distillation column under distillation conditions of temperature and pressure selected to provide a first lighter liquid distillation fraction comprising $C_5$ hydrocarbons, methyl formate, acetaldehyde and a first heavier liquid distillation fraction comprising propylene oxide, water, methanol, tertiary butyl alcohol, acetone, acetaldehyde, propionaldehyde and $C_6$ hydrocarbons, charging the first heavier distillation fraction to a second distillation column and operating the second distillation column under distillation conditions of temperature and pressure selected to provide a second lighter liquid distillation fraction comprising propylene oxide, less than half of the water charged to the second distillation column, more than half of the methanol charged to the second distillation column, methyl formate, acetaldehyde and $C_6$ hydrocarbons, and a second heavier liquid distillation fraction comprising more than half of the water charged to the second distillation column, less than half of the methanol charged to the second distillation column, acetone, tertiary butyl alcohol and propionaldehyde, charging the second lighter distillation fraction to a third extractive distillation column and also charging an effective amount of a $C_8$ to $C_{10}$ paraffinic hydrocarbon extractive distillation agent thereto and operating the third distillation column under extractive distillation conditions of temperature and pressure selected to provide a third lighter liquid distillation fraction comprising the extractive distillation agent, substantially less than 50% of the water charged to the third distillation column, substantially all of the methanol charged to the third distillation column, methyl formate and acetaldehyde and a third heavier liquid distillation fraction comprising propylene oxide, less than half of the water charged to the third distillation column, and $C_6$ hydrocarbons, charging the third heavier distillation fraction to a fourth extractive distillation column and also charging an effective amount of a $C_8$ to $C_{10}$ paraffinic hydrocarbon extractive distillation agent hereto and operating the fourth distillation column under extractive distillation conditions of temperature and pressure selected to provide a fourth lighter vapor overhead distillate fraction comprising propylene oxide and less than half of the water charged to the fourth distillation column and a fourth heavier liquid distillation fraction comprising the extractive distillation agent, more than half of the water charged to the fourth distillation column, and $C_6$ hydrocarbons, passing said propylene oxide vapor fraction through a drying chamber containing a porous hygroscopic solid absorbent at a temperature of about 34° to about 100° C. and a pressure of about 15 to about 30 psia, to selectively absorb water vapor onto the absorbent, and liquefying and recovering the thus-dehydrated purified propylene oxide.

15. A method as in claim 14 wherein the porous hygroscopic solid absorbent is a molecular sieve.

16. A method as in claim 14 wherein the porous hygroscopic solid absorbent is a hygroscopic alkali metal or alkaline earth metal oxide or a hygroscopic alkali metal or alkaline earth metal hydroxide compound.

17. A method as in claim 14 wherein the porous hygroscopic solid absorbent is a hygroscopic alkali metal sulfate or an alkaline earth metal sulfate.

* * * * *